United States Patent
Rabe et al.

(10) Patent No.: US 6,555,097 B1
(45) Date of Patent: *Apr. 29, 2003

(54) COSMETIC PRODUCT SYSTEMS COMPRISING A TRANSFER RESISTANT, FLEXIBLE FILM-FORMING COSMETIC PRODUCT AND AN OIL-CONTAINING COMPOSITION

(75) Inventors: Thomas Elliot Rabe, Baltimore, MD (US); Lee Ellen Drechsler, Cincinnati, OH (US); Edward Dewey Smith, III, Mason, OH (US); Terutomo Dohmae, Shiga (JP); Christina M. Hines, Houston, TX (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 09/322,436

(22) Filed: May 28, 1999

Related U.S. Application Data

(63) Continuation of application No. 08/862,524, filed on May 23, 1997, now Pat. No. 6,019,962, which is a continuation-in-part of application No. 08/732,944, filed on Oct. 17, 1996, now abandoned

(60) Provisional application No. 60/008,552, filed on Dec. 13, 1995, and provisional application No. 60/006,273, filed on Nov. 7, 1995.

(51) Int. Cl.[7] .............................................. A61K 7/025
(52) U.S. Cl. ....................... 424/64; 424/401; 424/63; 424/69; 424/70.12; 424/78.03; 424/DIG. 5; 514/844
(58) Field of Search ................... 424/401, 63, 64, 424/69, 70.12, 78.03, DIG. 5; 514/844

(56) References Cited

U.S. PATENT DOCUMENTS

| | | |
|---|---|---|
| 2,678,893 A | 5/1954 | Kauppi ................. 117/135.5 |
| 2,681,878 A | 6/1954 | Kauppi ..................... 167/22 |
| 3,600,186 A | 8/1971 | Mattson et al. ................. 99/1 |
| 3,642,635 A | 2/1972 | MacLeod ..................... 252/59 |
| 3,836,647 A | 9/1974 | Lange ........................ 424/184 |
| 3,857,805 A | 12/1974 | Prickril .................. 260/28.5 B |
| 4,005,195 A | 1/1977 | Jandacek .................... 424/180 |
| 4,005,196 A | 1/1977 | Jandacek et al. ........... 424/180 |
| 4,946,302 A | 8/1990 | Uchida ....................... 401/288 |
| 5,106,625 A | 4/1992 | Yamamoto et al. ......... 424/401 |
| 5,462,737 A | 10/1995 | Pfleuger ..................... 424/401 |
| 5,500,138 A | 3/1996 | Bacon et al. ................. 252/8.8 |
| 5,500,154 A | 3/1996 | Bacon et al. ................. 252/551 |
| 5,505,937 A * | 4/1996 | Castrogiovanni et al. |
| 5,512,272 A | 4/1996 | Krzysik ........................ 424/59 |
| 5,725,845 A | 3/1998 | Krog et al. .................... 424/64 |
| 5,800,816 A | 9/1998 | Brieva et al. ................. 424/63 |
| 6,019,962 A * | 2/2000 | Rabe et al. .................. 424/401 |
| 6,033,650 A * | 3/2000 | Calello et al. |
| 6,071,503 A * | 6/2000 | Drechsler et al. |

FOREIGN PATENT DOCUMENTS

| | | | |
|---|---|---|---|
| DE | 1913569 | 10/1969 | |
| DE | 38 37 473 | 5/1990 | ............ A61K/7/02 |
| DE | 4025040 | 2/1991 | ............ A61K/7/02 |
| EP | 0519727 | 12/1992 | ............ A61K/7/48 |
| EP | 0602905 | 6/1994 | .......... A61K/7/027 |
| EP | 0709083 | 5/1996 | ............ A61K/7/48 |
| EP | 0748622 | 12/1996 | .......... A61K/7/025 |
| GB | 2198037 | 6/1988 | .......... A46B/11/02 |
| GB | 2 197783 | 5/1990 | .......... A46B/11/02 |
| GB | 2211081 | 7/1991 | .......... A46B/11/02 |
| JP | 05-221829 | 8/1993 | .......... A61K/7/025 |
| WO | 97/01321 | 1/1997 | .......... A61K/7/021 |
| WO | 97/17057 | 5/1997 | ............ A61K/7/48 |

OTHER PUBLICATIONS

Leo, A. J., "Methods of Calculating Partition Coefficients", *Comprehensive Medicinal Chemistry*, (Eds., Hansch, Sammens, Taylor and Ransden), vol. 4, pp. 295–319, 1990.

Mark, J. E., *Physical Properties of Polymers Handbook*, AIP Press, Amer. Inst. of Physics, Chap. 16, pp. 227–239.

Vaughan, C. D., "Solubility Effects in Product, Package, Penetration and Preservation", *Cosmetics & Toiletries*, vol. 103, pp. 47–69, 1988.

General Electric, GE Silicones, Patent Technology, 7 pp.

General Electric, GE Silicones, Preliminary Data Sheet, 4 pp.

Patent Abstract of Japan, vol. 13, No. 24 (Feb. 19, 1989): JP63 230618A, Sep. 27, 1988.

\* cited by examiner

*Primary Examiner*—Jose' G. Dees
*Assistant Examiner*—Konata M. George
(74) *Attorney, Agent, or Firm*—Kenya T. Pierre; Dara M. Kendall; Tara M. Rosnell

(57) ABSTRACT

Cosmetic product systems comprise a transfer resistant, flexible film forming cosmetic product having a solubility parameter on the Hildebrand scale of less than or equal to 8.5 (calories/cm$^3$)$^{1/2}$, and a second composition comprising an oil having a C log P value greater than or equal to 13. The oil is selected from the group consisting of polyol fatty acid polyesters, triglycerides, glycerin/diethylene glycol/adipate cross polymers and mixtures thereof.

23 Claims, No Drawings

COSMETIC PRODUCT SYSTEMS COMPRISING A TRANSFER RESISTANT, FLEXIBLE FILM-FORMING COSMETIC PRODUCT AND AN OIL-CONTAINING COMPOSITION

CROSS REFERENCE

This is a continuation of application Ser. No. 08/862,524 filed May 23, 1997, now U.S. Pat. No. 6,019,962, which is a continuation-in-part of application Ser. No. 08/732,944 filed on Oct. 17, 1996, now abandoned that claimed priority under Title 35, United States Code 119(e) to Provisional Application Serial No. 60/006,273, filed Nov. 7, 1995 and Provisional Application Serial No. 60/008,552, filed Dec. 13, 1995.

TECHNICAL FIELD

The invention is for compositions and method for using said compositions to improve the performance of long-wearing cosmetic products. These compositions and methods for using such compositions enable the user to significantly enhance the attributes of long-wearing cosmetic products without compromising their primary advantages.

BACKGROUND ART

Compositions used to enhance cosmetic products are known in the art. Such compositions include those that are applied over top compositions such as lipstick to provide attributes such as gloss, lubricity and transfer-resistance of the cosmetic product they are applied over. These enhancement products utilize a variety of polymeric fluids and film forming technologies. For example, acrylic film-formers that are incorporated in lipstick overcoat products such as CSI Incorporated's "Sealed with a Kiss" are delivered in a volatile vehicle, alcohol, which is spread over the lipstick surface.

Alternative topcoat products to those described above are disclosed in Japanese Patent Application Number HEI 5[1993]221829, published Aug. 31, 1993. Said overcoats are reputed to exhibit improved durability of makeup effect, suppression of color transfer, and improved applicability. Said topcoats comprise from 0.2 to 25% of silica powder and/or alumina powder and from 75% to 99.8% of a perfluoropolyether of general formula:

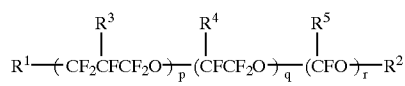

wherein $R^1$ though $R^5$ are independent fluorine atoms, perfluoroalkyl groups, or oxyperfluoroalkyl groups; the value of p, q, and r is at least zero; wherein the perfluoropolyether molecular weight is from about 500 to about 10,000, wherein P, Q and R may be equal, but, not zero. The preferred perfluoropolyether disclosed therein is a commercially available product known as Fomblin HC-04, HC-25, and HC-R available from Montefluosu of Milano, Italy.

While such compositions may provide certain advantages, it has been found that they often disrupt the primary advantages of the cosmetic products they are applied over. For example, cosmetic products compromise their gloss or feel attributes in order to improve the long wear properties provided by the composition that is applied over top the cosmetic product. Alternately, cosmetic products must sacrifice long wear properties in order to improve the gloss and or feel attributes provided by the such compositions.

SUMMARY OF THE INVENTION

The present invention is for compositions and methods for using said compositions with cosmetic products having a solubility parameter less than or equal to 8.5 (calories/cm$^3$)$^{1/2}$ in order to improve the overall performance associated with the cosmetic product. These compositions comprise oils having a C log P value greater than or equal to 13.

Additionally, the present invention covers a method of improving transfer resistant, flexible film-forming cosmetic product wherein said method comprises the steps of:

a. applying a transfer resistant, flexible film-forming cosmetic product wherein said cosmetic product has a solubility parameter less than or equal to 8.5 (calories/cm$^3$)$^{1/2}$;

b. allowing said cosmetic product to dry; and c. applying over said cosmetic product a second composition wherein said second composition comprises an oil having a C log P value greater than or equal to 13.

BACKGROUND OF THE INVENTION

When supplementing the benefits of a cosmetic product, the complimenting or second composition should minimize compromising said cosmetic product. The compositions of the present application may be used in conjunction with all types of cosmetic products wherein it is desirable to provide additional attributes. In the case of lip products, such attributes include gloss, shine and lubricity.

Specifically in context of film-forming cosmetic products, the second composition should be incompatible with the cosmetic product. By incompatible it is meant that the compositions of the present invention comprise specific components that do not disrupt the film formed after application of said cosmetic product. This is particularly the case for transfer-resistant, flexible film-forming cosmetic products such as lip cosmetics.

Lip cosmetics are well known in the art and can encompass a number of different formulations in order to provide both cosmetic and skin care benefits to the skin. One benefit that has been most often sought by consumers, particularly in lip cosmetic product, is increased or "long" wear.

Long wearing cosmetic products are considered by some to be those that are resistant to blotting on to another object that comes in contact with the cosmetic product; for example, resistance to lip composition coming off onto table wear such as cups and napkins. However, other factors found to be critical in predicting long wear is the ability of the cosmetic product to be flexible and resistant to solvents such as food oils once applied to the skin. Such cosmetic products are the subject matter of co-pending patent applications USSN 08/732,946 and USSN 08/732,948, now U.S. Pat. No. 6,071,503. "Transfer Resistant Cosmetic Compositions", Drechsler et al., both filed Oct. 17, 1996; both incorporated herein by reference. Such compositions comprise organosiloxane resins, fluid diorgansiloxane polymers, and a volatile carrier wherein the film formed upon application of the cosmetic product is substantially transfer-resistant and flexible wherein the cosmetic product has surprisingly increased wear.

In one embodiment, such cosmetic compositions comprise (A) a mixture of (1) an organosiloxane resin and (2) a fluid diorganopolysiloxane polymer, wherein the ratio of (1) to (2) is from about 1:1 to about 20:1 when (2) has a viscosity from about 1,000 to about 200,000 cSt at 25° C., and a ratio of (1) to (2) from about 1:9 to about 20:1 when (2) has a viscosity greater than 200,000 cSt at 25° C.; and (B) a volatile carrier.

The cosmetic products used in conjunction with the composition of the present invention have solubility parameters less than or equal to about 8.5 (calories/cm$^3$)$^{1/2}$ on the Hildebrand scale. In general, the solubility parameter is a function of the cohesive energy of the materials or the cosmetic product comprising said materials. Cohesive energy is simply an attractive force that is dependent on the electro-negativities of the atoms making up a molecule and serves as the basis for properties such as viscosity, adhesion, miscibility and even the boiling point. Some materials, like water, have high cohesive energy; some, like oil, have low cohesive energy. Highly cohesive ingredients are "polar", while those less cohesive are oily or "non-polar". Hildebrand developed a method for deriving the solubility parameter from the boiling point, molecular weight and specific gravity of a material; J. H. Hildebrand, J. M. Prausnitz and R. L. Scott, Regular and Related Solutions, New York; Van Nostrand Reinholdt (1950), herein incorporated by reference. This Hildebrand solubility parameter is published for many cosmetic and pharmaceutical materials in the Cosmetic Bench Reference, Carol Stream Ill., Allured Publishing (1992) and in A. F. Barton, Handbook of Solubility Parameters and Other Cohesion Parameters, 2nd ed., Boca Raton; CRC Press (1992); both incorporated herein by reference.

The C log P value of the oils in said composition determines whether the composition of the present invention is sufficiently incompatible with the cosmetic product in order to improve the cosmetic products performance. The value P is the octanol/water partitioning coefficient of the oils comprising said composition. The octanol/water partitioning coefficient is the ratio between said compositions equilibrium concentration in octanol and in water. Since the values of the octanol/water partitioning coefficient are high, they are more conveniently given in the form of the logarithm to the base 10, or log P.

The log P values above are calculated using the "C log P" program available from Daylight CIS. This calculated logarithm of P is based on the fragment approach of Hansch and Leo (cf., A. Leo, in Comprehensive Medicinal Chemistry, Vol. 4, C. Hansch, P. G. Sammens, J. B. Taylor and C. A. Ransden, Eds., p. 295, Pergamon Press, 1990); incorporated herein by reference. The fragment approach is based on the chemical structure of each oil ingredient, and takes into account the numbers and types of atoms, the atom conductivity, and chemical bonding. The C log P values are the most reliable and widely used estimates for this physiochemical property.

Compositions of the present invention comprise oils and may take forms ranging from solid to liquids. Regardless of the form, compositions of the present invention contains at lest one oil wherein the aggregate C log P value for all the non-solid molecular entities is about that of the oil alone. The C log P value of the oils in said composition are greater than or equal to 13, preferably greater than or equal to 17, and most preferably greater than or equal to 20. The oils used in the present invention are selected from the group consisting of polyol fatty acid polyester, triglycerides, fluid synthetic polymers and mixtures thereof.

Polyol Fatty Acid Polyesters

Polyol fatty acid polyesters are fatty acid polyesters derived from any aliphatic or aromatic polyol that has at least 4 free hydroxyl groups, of which at least 80% of these free hydroxy groups are then esterified with one or more fatty acids having from 8 to 22 carbon atoms.

The polyol from which the polyol fatty acid polyesters are derived are preferably chosen from sugar polyols that comprise mono-, di, and polysaccharides. Preferred examples of monosaccharide sugar polyols include:

Pentose sugar polyols such as D-ribose, D-arabinose, D-xylose, D-lyxose, D-ribulose and D-xylulose;

Hexose sugars polyols such as D-allose, D-altrose, D-glucose, D-mannose, D-gulose, D-idose, D-galactose, D-talose, D-fructose, D-sorbose and D-tagatose;

Heptose sugar polyols such as D-mannoheptulose and D-sedoheptulose;

The polyol from which the polyol fatty acid polyesters are derived can also be chosen from disaccharides such as maltose, lactose, celloblose, sucrose, trehalose, gentioblose, meliblose and primeverose.

The polyol from which the polyol fatty acid polyesters are derived can also be chosen from tri-saccharides such as gentianose and raffinose.

The polyol from which the polyol fatty acid polyesters are derived can alternatively be chosen from sugar alcohols such as D-mannitol, D-sorbitol, D-ribitol, D-erithritol, D-lactitol and d-xylitol.

The polyol from which the polyol fatty acid polyesters are derived can also alternatively be chosen from sugars such as methyl glucoside and inositol. The preferred sugar polyol is sucrose. The sucrose polyol fatty acid esters or SPEs are disclosed in the priority document cited in the specification and are derived from sucrose and vegetable oil. This has been extensively disclosed in the patent literature in context of a non-digestible oils, including but not limited to U.S. Pat. Nos. 3,600,186, issued Aug. 17, 1971; 4,005,195, issued Jan. 25, 1977; 4,005,196, issued Jan. 25, 1977; all assigned to the Procter & Gamble Company and all herein incorporated by reference.

The fatty acids that are employed to form the polyol fatty acid polyesters disclosed herein can be individual free fatty acids having from 8 to 24, preferably 16 to 22 carbon atoms in the fatty acid molecule. These fatty acids can be saturated or unsaturated, linear or branched chain fatty acids.

Fats and Oils

Fats and oils useful in the present invention are triacylglycerides or triglycerides formed by an esterification reaction of fatty acids with glycerol. While the distinction between fats and oils is arbitrary, fats are typically considered solid or plastic at room temperature while oils are liquid under these same conditions. The fatty acids which are subsequently esterified to form triglyceride fats and oils are most usually derived form marine, animals and plant sources. For more information regarding triglyceride oils, their sources and processing, refer to Bailey, "Industrial Oil and Fats Products", Interscience Publications; incorporated herein by reference.

At least 90% of the ester substitution on the triglyceride backbone has carbon chain lengths of at least 12. The oils frequently are hydrogenated to some extent to deter rancidity. Such triglycerides include plant derived oils such as soy bean oil, castor bean oil, olive oil, sunflower oil, almond oil, peanut oil, canola oil, corn oil, other similarly related vegetable oils and mixtures thereof.

Synthetic Polymer Oils

Synthetic polymer oils are useful in the present invention. Said synthetic polymer oils are liquid at room temperature and include glycerin/diethylene glycol/adipate crosspolymers, available as Lexorez 100 from Inolex Chemical Company.

Optional Ingredients

There are a great number of other ingredients approved for use in the cosmetic art that may be used in compositions of the present invention. Such ingredients are those approved for use in cosmetics and can be found listed in reference books such as the CTFA Cosmetic Ingredient Handbook, Second Edition, The Cosmetic, Toiletries, and Fragrance Association, Inc. 1988, 1992. Said materials may be used provided their inclusion does not significantly disrupt the film formed once the cosmetic product has been applied to the skin. Said ingredients include waxes, fragrances, flavor oils, skin care ingredients such as sunscreen, emulsifiers and the like. Hypoallergenic compositions can be made into the present invention where said compositions do not contain fragrances, flavor oils, lanolin, sunscreens, particularly PABA, or other sensitizers and irritants. The additional ingredients that are added should not lower the aggregate C Log P values for the oils of the composition to less than 13.

As previously mentioned, oils are an important component of the present invention. In addition to said oils, other materials may be included to provide the product form desired by the consumer. Such forms include liquids, pastes, and solids. In the case of a solid form, the composition of the present invention comprises materials in a sufficient amount so as to form a stable stick. These materials are herein referred to as solid formers. Said solid formers are preferably used at levels from about 0.5% to about 35.0% more preferably from about 7.0% to about 25.0%, and most preferably from about 8% to about 20.0% of the composition. Said solid formers are selected from the group consisting of solid polyol fatty acid polyesters, waxes, solid oils and mixtures thereof.

a. Solid Polyol Polyesters

The solid polyol polyesters used in the present invention are polyol esters or polyesters wherein the fatty acid ester groups of the polyester comprise a combination of: (a) long chain unsaturated fatty acid moieties or a mixture of long chain unsaturated fatty acid moieties and short chain saturated fatty acid moieties, and (b) long chain saturated fatty acid moieties, the ratio of (a) to (b) being from about 1 to 15 to about 2 to 1. At least about 15%, preferably at least about 30%, more preferably at least about 50%, and most preferably at least about 60% by weight of the total fatty acid moieties of the polyesters are C20 or higher saturated fatty acid moieties. The long chain unsaturated fatty acid moieties are typically straight chain and contain at least about 12, preferably about 12 to about 22, more preferably about 18 to about 22 carbon atoms. The most preferred unsaturated fatty acids are the C18 mono and/or di unsaturated fatty acids. The short chain saturated fatty acids are typically unbranched and contain about 2 to about 12, preferably about 6 to about 12, and most preferably about 8 to about 12 carbon atoms. The long chain saturated fatty acids are typically straight chain and contain at least about 20, preferably about 20 to about 22, and most preferably about 22 carbon atoms. The molar ratio of Group (a) fatty acid moieties to Group (b) fatty acid moieties in the polyester molecule is from about 1:15 to about 2:1, preferably about 1:7 to about 5:3, and more preferably about 1:7 to about 3:5. The average degree of esterification of these fatty acid esters is such that at least about 60% of the hydroxyl groups of the polyol are esterified. In the case of sucrose polyesters from about 7 to about 8 of the hydroxyl groups of the polyol are preferably esterified. Typically, substantially all, e.g., at least about 85%, preferably at least about 95%, of the hydroxyl groups of the polyol are esterified. Preferred polyols of the solid polyol fatty acid esters are sugars selected from the group consisting of monosaccharides and disaccharides and trisaccharides, comprising from about 4 to about 11, preferably about 4 to about 8 and most preferably about 6 to about 8 hydroxyl groups. Examples of those containing four hydroxyl groups are the monosaccharides xylose, arabinose, and combinations thereof. Suitable five hydroxyl group-containing polyols are the monosaccharides galactose, fructose, mannose, glucose, and combinations thereof. Examples of disaccharide polyols which can be used include maltose, lactose, sucrose, and combinations thereof, all of which contain eight hydroxyl groups. The preferred polyol is sucrose.

Examples of long chain unsaturated fatty acid moieties include, but are not limited to, lauroleate, myristoleate, palmitoleate, oleate, elaidate, erucate, linoleate, linolenate, arachidonate, eicosapentaentoate, and docosahexaenoate. For oxidative stability, the mono- and diunsaturated fatty acid moieties are preferred.

Examples of suitable short chain saturated fatty acid moieties include, but are not limited to, acetate, caproate, caprylate, caprate, and laurate.

Examples of suitable long chain saturated fatty acid moieties include, but are not limited to, arachidate, behenate, lignocerate, and cerotate.

Of course, the long chain unsaturated fatty acid moieties can be used singly or in mixtures with each other or in mixtures with the short chain saturated fatty acid moieties, in all proportions. Likewise, the long chain saturated fatty acid moieties can be used in combination with each other in all proportions. Mixed fatty acid moieties from source oils which contain substantial amounts of the desired unsaturated or saturated acids can be used as the acid moieties to prepare compounds for use herein. The mixed fatty acids from the oils should contain at least about 30%, preferably at least about 50%, and most preferably at least about 80% of the desired unsaturated or saturated acids. For example, rapeseed oil fatty acids or soybean oil fatty acids can be used instead of pure C12–C16 unsaturated fatty acids. Hardened, i.e. hydrogenated, high erucic rapeseed oil fatty acids can be used instead of pure C20–C22 saturated acids, Preferably the C20 and higher acids, or their derivatives, e.g. methyl or other low alkyl esters, are concentrated for example by distillation. The fatty acids from palm kernal oil or coconut oil can be used as a source of C8 to C12 acids, An example of the use of source oils to make solid polyol polyesters for use in the compositions herein is the preparation of solid sucrose polyester, employing the fatty acids of high oleic sunflower oil and substantially completely hydrogenated high erucic rapeseed oil. When sucrose is substantially completely esterified with a 1:3 by weight blend of the methyl esters of the fatty acids of these two oils, the resulting sucrose polyester will have a molar ratio of unsaturated C18 acid radicals to C20 and higher saturated acid radicals of about 1:1 and about 28.6 weight percent of the total fatty acids in the polyester will be C22 fatty acids.

The higher the proportions of the desired unsaturated and saturated acids in the fatty acid stocks used in making the solid polyol polyester, the more efficient the ester will be in its ability to bind with the liquid oils described hereinbelow.

Examples of solid polyol fatty acid polyesters for use in the composition herein include, but are not limited to, the octaester of raffinose in which the esterifying fatty acid moieties are linoleate and behenate in a 1:3 molar ratio; the heptaester of maltose wherein the esterifying fatty acid moieties are sunflower seed oil fatty acids and lignocerate in a 3:4 molar ratio; the octaester of sucrose wherein the esterifying fatty acid moieties are oleate and behenate in a 2:6 molar ratio; and the octaester of sucrose wherein the esterfying fatty acid moieties are laurate, linoleate and behenate in a 1:3:4 molar ratio. A preferred material is sucrose polyester in which the degree of esterification is 7-8, and in which the fatty acid moieties are C18 mono- and/or di-unsaturated and behenic, in a molar ratio of unsaturates-:behenic of 1:7 to 3:5. A particularly preferred polyol ester is the octaester of sucrose in which there are about 7 behenic fatty acid moieties and about 1 oleic moiety in the molecule.

The solid fatty acid polyesters herein can be made according to prior art known methods for preparing polyesters of polyols. See, for example U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al., issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety.

b. Waxes

The waxes useful in the present invention are herein defined as organic mixtures or compounds of high molecular weight, solid at room temperature. Generally waxes are similar in composition to fats and oils except that they contain no glycerides. Waxes include high molecular weight hydrocarbons, fatty acids, fatty acid esters, fatty alcohols and mixtures thereof. Waxes useful in the present invention include wax generally known for use in the cosmetic arts. Such waxes include those disclosed in U.S. Pat. No. 5,599,547 Bartholomey et al., issued Feb. 4, 1997; herein incorporated by reference.

Suitable fatty acids have from about 10 to about 40 carbon atoms. Examples of which include 12-hydroxystearic acid, 12-hydroxylauric acid, 16-hydroxyhexadecanoic acid, behenic acid, eurcic acid, stearic acid, caprylic acid, lauric acid, isostearic acid, and mixtures thereof. Further examples of some suitable fatty acids are further described in U.S. Pat. 5,429,816, issued to Hofrichter et al. on Jul. 4, 1995; and U.S. Pat. 5,552,136, issued to Motley on Sept. 3, 1996, which descriptions are incorporated herein by reference.

Suitable fatty alcohol waxes for use herein include monohydric alcohols, ethoxylated fatty alcohols, and fatty alcohol esters, excluding the ethoxylated fatty alcohols and fatty alcohol esters useful as emulsifiers herein. Specific examples of commercially available fatty alcohols include, but are not limited to, Unilin 550, Unilin 700, Unilin 425, Unilin 400, Unilin 350, and Unilin 325, all supplied by Petrolite. Suitable ethoxylated fatty alcohols include, but are not limited, Unithox 325, Unithox 400, and Unithox 450, Unithox 480, Unithox 520, Unithox 550, Unithox 720, Unithox 750, all of which are available from Petrolite. Non-limiting examples of suitable esters of fatty alcohols include tri-isostearyl citrate, ethyleneglycol di-12-hydroxystearate, tristearylcitrate, stearyl octanoate, stearyl heptanoate, trilaurylcitrate.

Suitable fatty acid ester waxes for use herein include ester waxes, monoglycerides, diglycerides, triglycerides and mixtures thereof. Non-limiting examples of suitable ester waxes include stearyl stearate, stearyl behenate, palmityl stearate, stearyl octyldodecanol, cetyl esters, cetearyl behenate, behenyl behenate, ethylene glycol distearate, ethylene glycol dipalmitate, and beeswax. Examples of commercial ester waxes include Kester waxes from Koster Keunen, Crodamol SS from Croda and Demalcare SPS from Rhone Poulenc.

Other waxes useful in the present invention are selected from the group consisting of animal waxes, vegetable waxes, mineral waxes, various fractions of natural waxes, synthetic waxes, petroleum waxes, ethylenic polymers, hydrocarbon types such as Fischer-Tropsch waxes, silicone waxes, and mixtures thereof wherein the waxes have a melting point greater than about 30° C. Waxes useful in the present invention are selected from the group consisting of synthetic waxes, ozokerite, jojoba esters, "Unilins", available from Petrolite Corporation, fatty alcohols from C22 to C50 and mixtures thereof. Synthetic waxes include those disclosed in Warth, *Chemistry and Technology of Waxes*, Part 2, 1956, Reinhold Publishing; herein incorporated by reference. The waxes most useful herein have melting points from about 30° C. to about 115° C. and are selected from the $C_8$ to $C_{50}$ hydrocarbon waxes. Such waxes include long chained polymers of ethylene oxide combined with a dihydric alcohol, namely polyoxyethylene glycol. Such waxes include carbowax available from Carbide and Carbon Chemicals company. Other synthetic waxes include long-chained polymers of ethylene with OH or other stop length grouping at end of chain. Such waxes include the Fischer-Tropsch waxes as disclosed in the text disclosed above at pages 465–469 and include Rosswax, available from Ross company and PT-0602 available from Astor Wax Company. Additional synthetic waxes include the class of alkylated polyvinyl pyrrolidones or PVP, including tricontanyl PVP (available as Gannex WP-660 from ISP Company) and PVPIEicosene Copolymer (available as from ISP Company).

Specific waxes useful in the present invention are selected from the group consisting of beeswax, lanolin wax, shellac wax (animal waxes); carnauba, candelilla, bayberry (vegetable waxes); ozokerite, ceresin, (mineral waxes); paraffin, microcrystalline waxes (petroleum waxes); polyethylene, (ethylenic polymers); polyethylene homopolymers (Fischer-Tropsch waxes); $C_{24-45}$ alkyl methicones (silicone waxes); and mixtures thereof. Most preferred are beeswax, lanolin wax, carnauba, candelilla, ozokerite, ceresin, paraffins, microcrystalline waxes, polyethylene, $C_{24-45}$ alkyl methicones, and mixtures thereof.

c. Solid Oils

Solid oils useful herein are those which have a melting point of above about 30° C. to about 250° C., preferably from about 37° C. to about 100° C., more preferably from about 37° C. to about 80° C. As used herein the term "solid oils" refers to any oil or oil-like materials which are solids or semi-solids at temperatures of from about 200° C. to about 25° C., and have a solubility in water of generally less than about 1% by weight at 25° C. Examples of suitable solid oils include, but are not limited to, petrolatum, highly branched hydrocarbons, fatty alcohols, fatty acid esters, vegetable oils, hydrogenated vegetable oils, polypropylene glycols, alpha-hydroxy fatty acids, fatty acids having from about 10 to about 40 carbon atoms, alkyl amides of di and/or tri-basic carboxylic acids, n-acyl amino acid derivatives, and mixtures thereof. Solid oils useful in the cosmetic composition of the present invention are further described in U.S. Pat. No. 4,919,934, to Deckner et al., issued Apr. 24 1990, which is incorporated herein by reference in its entirety.

Suitable highly branched hydrocarbons for use herein include hydrocarbon compounds having from about 17 to about 40 carbon atoms. Nonlimiting examples of these hydrocarbon compounds include squalane, cholesterol, lanolin, docosane (i.e. a $C_{22}$ hydrocarbon), and isoparaffins.

Vegetable oils and hydrogenated vegetable oils which are solid or semi-solid at ambient temperatures of from about 20° C. to about 25° C. are also useful herein. Examples of suitable vegetable oils and hydrogenated vegetable oils include butterfat, chicken fat, goose fat, horse fat, lard (fatty tissue) oil, rabbit fat, sardine oil, tallow (beef), tallow (mutton), chinese vegetable tallow, babassu oil, cocoa butter, coconut oil, palm oil, palm kernal oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, derivatives thereof and mixtures thereof.

Suitable polypropylene glycols for use herein include $C_4$–$C_{16}$ alkyl ethers of polypropylene glycols, and $C_1$–$C_{16}$ carboxylic acid esters of polypropylene glycols. Nonlimiting examples of these materials include PPG-14 butyl ether, PPG-15 stearyl ether, PPG-9, PPG-12, PPG-15, PPG-17, PPG-20, PPG-26, PPG-30, PPG-34, and mixtures thereof.

Suitable alkyl amides of di and/or tri-basic carboxylic acids for use herein include disubstituted or branched monoamides, monosubstituted or branched diamides, triamides, and mixtures thereof. Some specific examples of alkyl amides of di- and tri-basic carboxylic acids include, but are not limited to, alkyl amides of citric acid, tricarballylic acid, aconitic acid, nitrilotriacetic acid and itaconic acid such as 1,2,3-propane tributylamide, 2-hydroxy-1,2,3-propane tributylamide, 1-propene-1,2,3-trioctylamide, N,N', N"-tri(methyldecylamide)amine, 2 docecyl-N,N'-dibutylsuccinamide, and mixtures thereof. Other suitable amides include the n-acyl amino acid derivatives described in U.S. Pat. 5,429,816, issued to Hofrichter et al. on Jul. 4, 1995.

2. Colorants

While the composition of the present invention is typically transparent, colorants including pigments and particulates such talc and mica may be used to add desirable effects to the cosmetic product. Colorants suitable for use herein are all inorganic and organic colors/pigments suitable for use in lip composition compositions. These include are usually aluminum, barium or calcium salts or lakes. Lakes are either a pigment that is extended or reduced with a solid diluent or an organic pigment that is prepared by the precipitation of a water-soluble dye on an adsorptive surface, which usually is aluminum hydrate. A lake also forms from precipitation of an insoluble salt from an acid or basic dye. Calcium and barium lakes are also used herein.

Preferred lakes of the present invention are Red 3 Aluminum Lake, Red 21 Aluminum Lake, Red 27 Aluminum Lake, Red 28 Aluminum Lake, Red 33 Aluminum Lake, Yellow 5 Aluminum Lake, Yellow 6 Aluminum Lake, Yellow 10 Aluminum Lake, Orange 5 Aluminum Lake and Blue 1 Aluminum Lake, Red 6 Barium Lake, Red 7 Calcium Lake.

Other colors and pigments can also be included in the lip compositions, such as pearls, titanium oxides, Red 6, Red 21, Blue 1, Green 5, Orange 5 dyes, chalk, talc, iron oxides and titanated micas.

3. Emulsifiers

Emulsifiers may be used as coupling agents which have an affinity for the hydrophilic and hydrophobic phases of lip compositions of this invention. Emulsifiers are also useful for incorporating polar fluids such as water, propylene glycol, glycerine or mixtures thereof. Such emulsifiers include those routinely used in cosmetics and are found in the CTFA. Polar fluids such as water, glycerine, propylene glycol and mixtures thereof may also be incorporated without an emulsifier when amphiphilic materials such as polyol fatty acid polyesters are used in the composition.

4. Skin Care Active Ingredients

Skin care active ingredients in both water soluble and water insoluble forms can be added to the lip composition. Said ingredients include fat soluble vitamins, sunscreens and pharmaceutically active ingredients. These skin care active ingredients include glycerine, zinc oxide; chamomile oil; ginko biloba extract; pyroglutamic acid, salts or esters; sodium hyaluronate; 2-hydroxyoctanoic acid; sulfur; salicylic acid; carboxymethyl cysteine, and mixtures thereof.

EXAMPLES

Examples of compositions of the present invention are as follows:

Example 1

| Ingredient | Weight (%) |
| --- | --- |
| SPE Cottonate | 89.75 |
| SPE Behenate | 5.05 |
| Sericite[1] | 5.05 |
| Propylparaben | 0.10 |
| Ethylene Brassylate | 0.05 |

1. Sericite available from U.S. Cosmetics Corporation

Combine all ingredients in a vessel and heat to 90° C. while stirring constantly with a propeller mixer. When the SPE Behenate has completely melted and the mixture is homogeneous, remove from heat and cool to room temperature. The mixture should be stirred constantly during cooling. Transfer the resulting fluid to individual packages.

Example 2

| Ingredient | Weight (%) |
| --- | --- |
| SPE Cottonate | 90.30 |
| SPE Behenate | 4.70 |
| Mica[1] | 4.65 |
| Propylparaben | 0.15 |
| Methyparaben | 0.15 |
| Ethylene Brassylate | 0.05 |

[1]. Sericite available from U.S. Cosmetics Corporation

Combine all ingredients in a vessel and heat to 90° C. while stirring constantly with a propeller mixer. When the SPE Behenate has completely melted and the mixture is homogeneous, remove from heat and cool to room temperature. The mixture should be stirred constantly during cooling. Transfer the resulting fluid to individual packages.

Example 3

| Ingredient | Weight (%) |
| --- | --- |
| Castor Oil | 89.75 |
| Glycerin/Diethylene Glycol/Adipate Crosspolymer[1] | 5.00 |
| Ozokerite | 5.00 |
| Propylparaben | 0.10 |
| Methyparaben | 0.10 |
| Ethylene Brassylate | 0.05 |

[1]. available as Lexorez 100 from Inolex Chemical Company.

Combine all ingredients in a vessel and heat to 90° C. while stirring constantly with a propeller mixer. When the ozokerite has completely melted and the mixture is homogeneous, remove from heat and cool to room temperature. The mixture should be stirred constantly during cooling. Transfer the resulting fluid to individual packages.

Example 4

| Ingredient | Weight (%) |
|---|---|
| SPE Cottonate | 85.85 |
| SPE Behenate | 14.00 |
| Propylparaben | 0.10 |
| Ethylene Brassylate | 0.05 |

Combine all ingredients in a vessel and heat to 90° C. while stirring constantly with a propeller mixer. When the SPE Behenate has completely melted and the mixture is homogeneous, remove from heat and pour into lipstick molds. Cool to approximately −5° C. before de-molding and placing in an appropriate package.

Example 5

| Ingredient | Weight (%) |
|---|---|
| Group A: | |
| SEFA Cottonate | 84.58 |
| SEFA Behenate | 14.36 |
| Ganex Wax WP-660[1] | 0.86 |
| Propylparaben | 0.10 |
| BHT | 0.05 |
| Group B: | |
| Ethylene Brassylate | 0.05 |

[1]. Ganex Wax available from ISP Technologies, Inc.

Combine Group A ingredients together and mix well with a spatula. Heat the Group A mixture until all solids melt (approx. 90° C.), stirring occasionally while heating. Add Group B ingredients and mix for 5 minutes with a propeller mixer. Do not let the temperature rise above 90° C. When the mixture of Groups A and B ingredients is homogeneous, pour the molten material into seasoned lipstick molds. Chill the filled molds at 5° C. for approximately 20 minutes. Remove the molds to ambient conditions and de-mold sticks. Place sticks in lipstick cases.

Example 6

| Ingredient | Weight (%) |
|---|---|
| Group A: | |
| SEFA Cottonate | 70.67 |
| SEFA Behenate | 14.13 |
| Talc | 15.00 |
| Propylparaben | 0.10 |
| BHT | 0.05 |
| Group B: | |
| Ethylene Brassylate | 0.05 |

Combine Group A ingredients together and mix well with a spatula. Heat the Group A mixture until all solids melt (approx. 90° C.), stirring occasionally while heating. Add Group B ingredients and mix for 5 minutes with a propeller mixer. Do not let the temperature rise above 900° C. When the mixture of Groups A and B ingredients is homogeneous, pour the molten material into seasoned lipstick molds. Chill the filled molds at 5° C. for approximately 20 minutes. Remove the molds to ambient conditions and de-mold sticks. Place sticks in lipstick cases.

Example 7

| Ingredient | Weight (%) |
|---|---|
| Group A: | |
| SEFA Cottonate | 83.17 |
| SEFA Behenate | 16.63 |
| Propylparaben | 0.10 |
| BHT | 0.05 |
| Group B: | |
| Ethylene Brassylate | 0.05 |

Combine Group A ingredients together and mix well with a spatula. Heat the Group A mixture until all solids melt (approx. 90° C.), stirring occasionally while heating. Add Group B ingredients and mix for 5 minutes with a propeller mixer. Do not let the temperature rise above 90° C. When the mixture of Groups A and B ingredients is homogeneous, pour the molten material into seasoned lipstick molds. Chill the filled molds at 5° C. for approximately 20 minutes. Remove the molds to ambient conditions and de-mold sticks. Place sticks in lipstick cases.

Example 8

| Ingredient | Weight (%) |
|---|---|
| Group A: | |
| SEFA Cottonate | 75.02 |
| SEFA Behenate | 13.55 |
| Talc | 7.50 |
| Ganex Wax WP-660[1] | 0.50 |
| Propylparaben | 0.15 |
| BHT | 0.05 |
| Group B: | |
| Glycerin | 3.00 |
| Methylparaben | 0.15 |
| Group C: | |
| Ethylene Brassylate | 0.05 |

[1]. Ganex Wax available from ISP Technologies, Inc.

Combine Group A ingredients together and mix well with a spatula. Heat the Group A mixture until all solids melt (approx. 90° C.), stirring occasionally while heating. Combine Group B ingredients together and mix well with a spatula. Heat the Group B mixture to approximately 90° C. Combine Group A and Group B mixtures and homogenize for 5 minutes at 5000 rpm. Add Group C ingredients and mix for 5 minutes with a propeller mixer. When the mixture is homogeneous, pour the molten material into seasoned lipstick molds. Chill the filled molds at 5° C. for approximately 20 minutes. Remove the molds to ambient conditions and de-mold sticks. Place sticks in lipstick cases.

Example 9

| Ingredient | Weight (%) |
|---|---|
| Group A: | |
| SEFA Cottonate | 59.55 |
| SEFA Behenate | 12.50 |
| Talc | 7.50 |
| Propylparaben | 0.15 |
| Vitamin E Linoleate | 0.10 |
| Group B: | |
| Water | 10.00 |
| Propylene Glycol | 5.00 |
| Glycerin | 5.00 |
| Methylparaben | 0.15 |
| Group C: | |
| Ethylene Brassylate | 0.05 |

Combine Group A ingredients together and mix well with a spatula. Heat the Group A mixture until all solids melt (approx. 90° C.), stirring occasionally while heating. Combine Group B ingredients together and mix well with a spatula. Heat the Group B mixture to approximately 90° C. Combine Group A and Group B mixtures and homogenize for 2 minutes at 5000 rpm. Add Group C ingredients and mix for 5 minutes with a propeller mixer. When the mixture is homogeneous, pour the molten material into seasoned lipstick molds. Chill the filled molds at 5° C. for approximately 20 minutes. Remove the molds to ambient conditions and de-mold sticks. Place sticks in lipstick cases.

Example 10

| Ingredient | Weight (%) |
|---|---|
| Group A: | |
| SEFA Cottonate | 85.85 |
| SEFA Behenate | 14.00 |
| Propylparaben | 0.10 |
| Group B: | |
| Ethylene Brassylate | 0.05 |

Combine Group A ingredients together and mix well with a spatula. Heat the Group A mixture until all solids melt (approx. 90° C.), stirring occasionally while heating. Add Group B ingredients and mix for 5 minutes with a propeller mixer. Do not let the temperature rise above 90° C. When the mixture of Groups A and B ingredients is homogeneous, pour the molten material into seasoned lipstick molds. Chill the filled molds at 5° C. for approximately 20 minutes. Remove the molds to ambient conditions and de-mold sticks. Place sticks in lipstick cases.

Example 11

| Ingredient | Weight (%) |
|---|---|
| Group A: | |
| SEFA Cottonate | 85.21 |
| SEFA Behenate | 14.09 |
| Ganex Wax WP-660[1] | 0.50 |
| Propylparaben | 0.10 |
| BHT | 0.05 |
| Group B: | |
| Ethylene Brassylate | 0.05 |

[1]. Ganex Wax available from ISP Technologies, Inc.

Combine Group A ingredients together and mix well with a spatula. Heat the Group A mixture until all solids melt (approx. 90° C.), stirring occasionally while heating. Add Group B ingredients and mix for 5 minutes with a propeller mixer. Do not let the temperature rise above 90° C. When the mixture of Groups A and B ingredients is homogeneous, pour the molten material into seasoned lipstick molds. Chill the filled molds at 5° C. for approximately 20 minutes. Remove the molds to ambient conditions and de-mold sticks. Place sticks in lipstick cases.

Example 12

| Ingredient | Weight (%) |
|---|---|
| Group A: | |
| SEFA Cottonate | 89.75 |
| SEFA Behenate | 5.05 |
| Mica | 5.05 |
| Propylparaben | 0.10 |
| Group B: | |
| Ethylene Brassylate | 0.05 |

Combine Group A ingredients together and mix well with a spatula. Heat the Group A mixture until all solids melt (approx. 90° C.), stirring occasionally while heating. Add Group B ingredients and mix for 5 minutes with a propeller mixer. Do not let the temperature rise above 90° C. When the mixture of Groups A and B ingredients is homogeneous, pour the molten material into individual containers. Allow to cool to ambient conditions.

Example 13

| Ingredient | Weight (%) |
|---|---|
| Group A: | |
| SEFA Cottonate | 89.00 |
| Candelilla Wax | 3.00 |
| Ozokerite | 1.00 |
| Microcrystalline Wax | 1.50 |
| Beeswax | 5.30 |
| Group B: | |
| BHT | 0.05 |

-continued

| Ingredient | Weight (%) |
|---|---|
| Ethylene Brassylate | 0.05 |
| Propylparaben | 0.10 |

Combine Group A ingredients together and mix well with a spatula. Heat the Group A mixture until all solids melt (approx. 90° C.), stirring occasionally while heating. Add Group B ingredients and mix for 5 minutes with a propeller mixer. Do not let the temperature rise above 90° C. When the mixture of Groups A and B ingredients is homogeneous, pour the molten material into seasoned lipstick molds. Chill the filled molds at 5° C. for approximately 20 minutes. Remove the molds to ambient conditions and de-mold sticks. Place sticks in lipstick cases.

Example 14

| Ingredient | Weigt (%) |
|---|---|
| Group A: | |
| SEFA Cottonate | 88.00 |
| Ozokerite | 6.00 |
| Beeswax | 5.80 |
| Group B: | |
| BHT | 0.05 |
| Ethylene Brassylate | 0.05 |
| Propylparaben | 0.10 |

Combine Group A ingredients together and mix well with a spatula. Heat the Group A mixture until all solids melt (approx. 90° C.), stirring occasionally while heating. Add Group B ingredients and mix for 5 minutes with a propeller mixer. Do not let the temperature rise above 90° C. When the mixture of Groups A and B ingredients is neous, pour the molten material into seasoned lipstick molds. Chill the filled molds at 5° C. for approximately 20 minutes. Remove the molds to ambient conditions and de-mold sticks. Place sticks in lipstick cases.

Example 15

| Ingredient | Weight % |
|---|---|
| Group A: | |
| Castor Oil | 89.80 |
| SEFA Behenate | 10.00 |
| Group B: | |
| BHT | 0.05 |
| Ethylene Brassylate | 0.05 |
| Propylparaben | 0.10 |

Combine all ingredients in a vessel and heat to 90° C. while stirring constantly with a propeller mixer. When the ozokerite has completely melted and the mixture is homogeneous, remove from heat and cool to room temperature. The mixture should be stirred constantly during cooling. Transfer the resulting fluid to individual packages.

Example 16

| Ingredient | Weight % |
|---|---|
| Group A: | |
| Castor Oil | 74.80 |
| SEFA Behenate | 25.00 |
| Group B: | |
| BHT | 0.05 |
| Ethylene Brassylate | 0.05 |
| Propylparaben | 0.10 |

Combine all ingredients in a vessel and heat to 90° C. while stirring constantly with a propeller mixer. When the ozokerite has completely melted and the mixture is homogeneous, remove from heat and cool to room temperature. The mixture should be stirred constantly during cooling. Transfer the resulting fluid to individual packages.

The following are non-all encompassing examples of cosmetic products that may be used with the above compositions of the present invention:

Example 1

Lip Cosmetic Product

| Ingredients | Weight (%) |
|---|---|
| Group A: | |
| Silicone Gum[1] | 12.60 |
| Isododecane[2] | 12.60 |
| Group B: | |
| Isododecane[2] | 43.38 |
| Bentonite Clay[4] | 1.00 |
| Propylene Carbonate | 0.32 |
| Red #6 Calcium Lake | 1.00 |
| Red #7 Barium Lake | 3.00 |
| Titanium Dioxide | 1.50 |
| Mica | 2.20 |
| Organosiloxane resin[3] | 22.40 |

[1]. 2,500,000 cSt Dimethicone Gum available as SE 63 from General Electric.
[2]. Permethyl 99A available from Permethyl Corp.
[3]. MQ Resin (0.7:1 ratio M:Q) available as 1170-002 from General Electric.
[4]. Bentone 38 available from Rheox.

Combine Group A ingredients together in a beaker and mix with a propeller mixer until uniform. Combine all Group B ingredients except the propylene carbonate and hand-mix to roughly incorporate the dry powders. Homogenize the entire formulation using a Ross ME 100 LC homogenizer at about 7500 rpm until all pigments are fully dispersed. Next, while continuing the homogenization process, slowly add the propylene carbonate until mixture thickens. Combine Group A mixture with Group B mixture in a beaker and mix with a propeller mixer until uniform. Transfer the resulting fluid to individual packages.

Example 2

Liquid Foundation Cosmetic Product

| Ingredient | Weight (%) |
|---|---|
| Group A: | |
| Organosiloxane Resin[1] | 4.48 |
| Cyclomethicone[2] | 11.11 |
| Silicone-polyether Emulsifier[3] | 10.00 |
| Group B: | |
| Silicone-Treated Titanium Dioxide | 6.50 |
| Silicone-Treated Yellow Iron Oxide | 0.28 |
| Silicone-Treated Red Iron Oxide | 0.15 |
| Silicone-Treated Black Iron Oxide | 0.06 |
| Group C: | |
| 2,500,000 cSt Silicone Gum[4] | 2.52 |
| Cyclomethicone2 | 4.90 |
| Group D: | |
| Water | 49.50 |
| Glycerin | 10.00 |
| Methyl Paraben | 0.20 |
| 2-Phenoxyethanol | 0.30 |

[1]. MQ Resin available as 1170-002 from General Electric.
[2]. Cyclomethicone available as 245 fluid from Dow Corning.
[3]. Silicone-Polyether Emulsifier available as DC3225C from Dow Corning.
[4]. Dimethicone Gum (2,500,000 cSt) available as SE63 from General Electric.

Combine Group A and Group B ingredients together and homogenize at 9500 rpm for 15 minutes. Add Group C ingredients and homogenize at 2000 rpm for 2 minutes. Combine Group D ingredients in a separate container and mix with a propeller mixer until a clear solution forms. Add the Group D solution to the mixture of Groups A, B, and C very slowly while homogenizing at 2000 rpm. When all of the Group D solution has been incorporated, homogenize the entire mixture at 2000 rpm for an additional 10 minutes. Finally, homogenize the entire mixture at 5000 rpm for 5 minutes. Transfer the resulting fluid to individual packages.

Example 3

Mascara Cosmetic Product

| Ingredient | Weight (%) |
|---|---|
| Group A: | |
| Organosiloxane Resin[1] | 9.60 |
| Cyclomethicone[2] | 8.82 |
| Silicone-polyether Emulsifier[3] | 10.00 |
| Group B: | |
| Silicone-Treated Black Iron Oxide | 5.00 |
| Group C: | |
| 2,500,000 cSt Silicone Gum[4] | 5.40 |
| Cyclomethicone[2] | 16.19 |
| Group D: | |
| Water | 43.50 |
| Sodium Chloride | 1.00 |
| Methyl Paraben | 0.20 |
| 2-Phenoxyethanol | 0.30 |

[1]. MQ Resin available as 1170-002 from General Electric.
[2]. Cyclomethicone available as 244 fluid from Dow Corning.
[3]. Silicone-Polyether Emulsifier available as DC3225C from Dow Corning.
[4]. Dimethicone Gum (2,500,000 cSt) available as SE63 from General Electric.

Combine Group A and Group B ingredients together and homogenize at 9500 rpm for 15 minutes. Add Group C ingredients and homogenize at 2000 rpm for 2 minutes. Combine Group D ingredients in a separate container and mix with a propeller mixer until a clear solution forms. Add the Group D solution to the mixture of Groups A, B, and C very slowly while homogenizing at 2000 rpm. When all of the Group D solution has been incorporated, homogenize the entire mixture at 2000 rpm for an additional 10 minutes. Finally, homogenize the entire mixture at 5000 rpm for 5 minutes. Transfer the resulting fluid to individual packages.

Example 4

Shear Lip Tint Cosmetic Product

| Ingredients | Weight (%) |
|---|---|
| Group A: | |
| Silicone Gum[1] | 11.88 |
| Isododecane[2] | 54.45 |
| Group B: | |
| Organosiloxane resin[3] | 20.78 |
| Red #6 Calcium Lake | 0.50 |
| Red #7 Barium Lake | 0.50 |
| Gemtone Sunstone[5] | 0.50 |
| Timiron MP-115 Pearl[6] | 0.50 |
| Bentone Gel[4] | 10.89 |

[1]. 2,500,000 cSt Dimethicone Gum available as SE 63 from General Electric.
[2]. Permethyl 99A available from Permethyl Corp.
[3]. MQ Resin (0.7:1 ratio M:Q) available as 1170-002 from General Electric.
[4]. VS-5 PC available from Rheox.
[5]. Gemtone Sunstone available from Mearl Corporation.
[6]. Timiron MP-115 Pearl available from Mearl Corporation.

Combine Group A ingredients together in a beaker and mix with a propeller mixer until uniform. Add Group B ingredients to the Group A mixture and hand-mix to roughly incorporate the dry powders. Homogenize the entire formulation until all pigments are fully dispersed. Transfer the resulting fluid to individual packages.

Example 5

Liquid Eye Liner Cosmetic Product

| Ingredient | Weight (%) |
|---|---|
| Group A: | |
| Organosiloxane Resin[1] | 8.90 |

-continued

| Ingredient | Weight (%) |
| --- | --- |
| Isododecane[2] | 14.90 |
| Group B: | |
| Black Iron Oxide | 20.00 |
| Propylparaben | 0.10 |
| Group C: | |
| 100,000 cSt Silicone Fluid[3] | 11.10 |
| Isododecane[2] | 33.00 |
| Group D: | |
| Isododecane[2] | 10.00 |
| Trihydroxystearin | 2.00 |

[1]. MQ Resin (0.7:1 ratio M:Q) available as 1170-002 from General Electric.
[2]. Permethyl 99A available from Permethyl Corp.
[3]. Dimethicone Fluid (100,000 cSt) available from General Electric.

Combine Group A ingredients together and mix with a propeller mixer until uniform. Add Group B ingredients and homogenize until pigments are fully dispersed. Premix Group C ingredients in a separate container using a propeller mixer until uniform, then combine with the mixture of Groups A and B ingredients. Premix Group D ingredients with heating to about 57–60° C. for about 3 minutes. Remove from the heat and homogenize for approximately 5 minutes or until a gel develops. Finally, add the Group D mixture to the rest of the batch and heat the entire mixture to 57–60° C. for about 7–10 minutes while mixing with a propeller mixer. Remove the batch from the heat and allow it to cool to room temperature while mixing with a propeller mixer. Transfer the resulting fluid to individual packages.

Example 6

Eye Shadow Cosmetic Product

| Ingredient | Weight (%) |
| --- | --- |
| Group A: | |
| Organosiloxane Resin[1] | 22.14 |
| Isododecane[2] | 14.90 |
| Group B: | |
| Flamenco Gold Pearl | 0.60 |
| Flamenco Superpearl | 0.84 |
| Titanium Dioxide | 0.94 |
| Gemtone Copper | 0.41 |
| Gemtone Sunstone | 1.21 |
| Propylparaben | 0.10 |
| Group C: | |
| 1,000 cSt Silicone Fluid[3] | 13.86 |
| Isododecane[2] | 33.00 |
| Group D: | |
| Isododecane[2] | 10.00 |
| Trihydroxystearin | 2.00 |

[1]. MQ Resin (0.7:1 ratio M:Q) available as 1170-002 from General Electric.
[2]. Permethyl 99A available from Permethyl Corp.
[3]. Dimethicone Fluid (1,000 cSt) available from General Electric.

Combine Group A ingredients together and mix with a propeller mixer until uniform. Add Group B ingredients and homogenize until pigments are fully dispersed. Premix Group C ingredients in a separate container using a propeller mixer until uniform, then combine with the mixture of Groups A and B ingredients. Premix Group D ingredients with heating to about 57–60° C. for about 3 minutes. Remove from the heat and homogenize for approximately 5 minutes or until a gel develops. Finally, add the Group D mixture to the rest of the batch and heat the entire mixture to 57–60° C. for about 7–10 minutes while mixing with a propeller mixer. Remove the batch from the heat and allow it to cool to room temperature while mixing with a propeller mixer. Transfer the resulting fluid to individual packages.

METHOD FOR IMPROVING COSMETIC PRODUCTS

The present invention covers a method of improving transfer resistant, flexible film-forming cosmetic product wherein said method comprises the steps of:

a. applying a transfer resistant, flexible film-forming cosmetic product to the skin wherein said cosmetic product has a solubility parameter less than or equal to 8.5 (calories/cm$^3$)$^{1/2}$;

b. allowing said cosmetic product to dry; and c. applying over said cosmetic product a second composition wherein said composition comprises an oil having a C log P value greater than or equal to 13.

The user applies both the cosmetic product and the composition of the present invention from a suitable cosmetic applicator. Applicators useful for fluid products include a liquid pen package disclosed in British Patent 21198037, issued May 9, 1990, assigned to Mitsubishi Pencil Co., Ltd. of Japan.

Another such cosmetic dispenser is a unidirectional twist-up dispensing device with incremental dosing as disclosed in co-pending patent application USSN 08/738,129, "Simplified Unidirectional Twist-Up Dispensing Device with Incremental Dosing", Horstman et al., filed Oct. 25, 1996 to Procter and Gamble. Such a twist-up dispensing device can include a hollow housing defining a chamber having an open dispensing end and a piston located within the chamber being limited to translational movement within the chamber. The piston preferably having a threaded rod extending therefrom that engages with a threaded aperture in an actuator such that advancement of the piston toward the dispensing end occurs when the actuator is rotated. Rotation of the actuator causes the product to be dispensed from the dispensing end. An applicator is preferably attached to the dispensing end of the housing in fluid communication with the chamber wherein the product is dispensed through the applicator. The applicator can comprise a ferrule and an application portion wherein the ferrule is attached to the dispensing end of the housing and the application portion has at least one orifice located therein. Several versions of applicators can be utilized including. for example, a fiber brush or an application surface having flocking thereon. Flocking is a mat of thin, short, plastic fibers substantially perpendicular to the application surface. The bristles of a fiber brush are preferably tapered and made of a plastic material. In addition, the complimentary composition may be formed into a solid and be delivered in a more traditional applicator or implement known in the art.

We claim:

1. A cosmetic product system comprising:

a. a transfer resistant, flexible film-forming cosmetic product having a solubility parameter on the Hildebrand scale of less than or equal to 8.5 (calories/cm$^3$)$^{1/2}$; and b. a second composition comprising an oil having a C log P value greater than or equal to 13, the oil being selected from the group consisting of polyol fatty acid polyesters, triglycerides, glycerin/diethylene glycol/adipate cross polymers, and mixtures thereof.

2. A cosmetic product system according to claim 1 wherein said second composition comprises at least about 55% of said oil.

3. A cosmetic product system according to claim 2 wherein said oil is a polyol fatty acid polyester comprising a fatty acid polyester derived from an aliphatic or aromatic polyol having at least 4 free hydroxyl groups, wherein at least 80% of the free hydroxyl groups are esterified with one or more fatty acids having from 8 to 22 carbon atoms.

4. A cosmetic product system according to claim 3 wherein said second composition comprises at least about 65% of said polyol fatty acid polyester.

5. A cosmetic product system according to claim 4 wherein the polyol of said polyol fatty acid polyester is a sugar polyol selected from the group consisting of monosaccharides, disaccharides, polysaccharides and mixtures thereof.

6. A cosmetic product system according to claim 5 wherein said sugar polyol is sucrose.

7. A cosmetic product system according to claim 1 wherein said oil is a triglyceride.

8. A cosmetic product system according to claim 7 wherein said triglyceride is plant derived.

9. A cosmetic product system according to claim 8 wherein said plant derived triglyceride is selected from the group consisting of soy bean oil, castor bean oil, olive oil, sunflower oil, almond oil, peanut oil, canola oil, corn oil, and mixtures thereof.

10. A cosmetic product system according to claim 1 wherein said second composition is a solid composition comprising said oil and a solid former.

11. A cosmetic product system according to claim 10 wherein said second composition comprises from about 0.5% to about 35% of said solid former and wherein said solid former is selected from the group consisting of polyol fatty acid polyesters, waxes, solid oils and mixtures thereof.

12. A cosmetic product system according to claim 11 wherein said solid former is a wax having a melting point greater than about 25° C. and selected from the group consisting of animal waxes, vegetable waxes, mineral waxes, fractions of natural waxes, synthetic waxes, petroleum waxes, hydrocarbon waxes, silicone waxes, and mixtures thereof.

13. A cosmetic product system according to claim 12 wherein said wax is selected from the group consisting of beeswax, lanolin wax, shellac wax, carnauba, candelilla, bayberry, ozokerite, ceresin, paraffin, microcrystalline waxes, polyethylene, polyethylene homopolymers, $C_{24-45}$ alkyl methicones and mixtures thereof.

14. A cosmetic product system according to claim 13 wherein said wax is a synthetic wax having a melting point of from about 30° C. to about 115° C. and selected from the group consisting of $C_8$ to $C_{50}$ hydrocarbon waxes, alkylated polyvinyl pyrrolidones, and polyoxyethylene glycol wax.

15. A cosmetic product system according to claim 14 wherein said solid former is a solid polyol polyester comprising a polyol ester and a polyester, wherein the fatty acid ester groups of the polyester comprise a combination of: (a) long chain unsaturated fatty acid moieties or a mixture of long chain unsaturated fatty acid moieties and short chain saturated fatty acid moieties, and (b) long chain saturated fatty acid moieties, the ratio of (a) to (b) being from about 1 to 15 to about 2 to 1.

16. A cosmetic product system according to claim 15 wherein said solid polyol polyester comprses a sugar selected from the group consisting of monosaccharides, disaccharides and trisaccharides, containing from about 4 to about 11 hydroxyl groups.

17. A cosmetic product system according to claim 16 wherein at least about 30% by weight of the total fatty acid moieties of said polyester is C20 or higher saturated fatty acid moieties.

18. A cosmetic product system according to claim 10 wherein said oil is a liquid, polyol fatty acid polyester and said solid former consists essentially of one or more waxes having a melting point greater than about 25° C.

19. A cosmetic product system according to claim 18 wherein said second composition comprises at least about 65% of said liquid, polyol fatty acid polyester and from about 0.5% to about 35% of said wax.

20. A cosmetic product system according to claim 1 wherein said cosmetic product comprises an organosiloxane resin, a fluid diorganopolysiloxane polymer, and a volatile carrier.

21. A cosmetic product system according to claim 20 wherein said cosmetic product, the ratio of organosiloxane (i) to fluid diorganopolysiloxane polymer (ii) is from about 1:1 to about 20:1 when (ii) has a viscosity from about 1,000 to about 200,000 cSt at 25° C., and from about 1:1 to about 20:1 when (ii) has a viscosity greater than 200,000 cSt at 25° C.

22. A cosmetic product system according to claim 1 wherein the cosmetic product system is a lip cosmetic system.

23. A cosmetic product system according to claim 22 wherein:
   a. said cosmetic product comprises an organosiloxane resin, a fluid diorganopolysiloxane polymer, and a volatile carrier, and wherein
   b. said second composition comprises at least about 55% of said oil, and wherein said oil is selected from the group consisting of polyol fatty acid polyesters, triglycerides, fluid synthetic polymers, and mixtures thereof.

* * * * *

UNITED STATES PATENT AND TRADEMARK OFFICE
CERTIFICATE OF CORRECTION

PATENT NO. : 6,555,097 B1
DATED : April 29, 2003
INVENTOR(S) : T.E. Rabe et al.

It is certified that error appears in the above-identified patent and that said Letters Patent is hereby corrected as shown below:

Column 22,
Line 13, "comprses" should read -- comprises --.

Signed and Sealed this

Twenty-second Day of March, 2005

JON W. DUDAS
*Director of the United States Patent and Trademark Office*